(12) United States Patent
Ding et al.

(10) Patent No.: US 8,168,060 B2
(45) Date of Patent: May 1, 2012

(54) SYSTEM AND METHOD FOR IMPROVING ACCURACY OF A GAS SENSOR

(75) Inventors: Yi Ding, Canton, MI (US); Richard E. Soltis, Saline, MI (US); Jacobus Hendrik Visser, Farmington Hills, MI (US); David John Kubinski, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 1333 days.

(21) Appl. No.: 11/757,684

(22) Filed: Jun. 4, 2007

(65) Prior Publication Data
US 2008/0296174 A1    Dec. 4, 2008

(51) Int. Cl.
*G01N 27/419* (2006.01)
(52) U.S. Cl. ........... 205/784.5; 205/784; 204/424; 204/425
(58) Field of Classification Search .......... 204/400–435; 205/775–794.5; 73/1.01–1.07; 702/85–107; 123/672–703
See application file for complete search history.

(56) References Cited

U.S. PATENT DOCUMENTS

| | | | | |
|---|---|---|---|---|
| 5,466,350 | A | * | 11/1995 | Baker et al. .................... 205/781 |
| 5,763,763 | A | | 6/1998 | Kato et al. |
| 5,879,525 | A | | 3/1999 | Kato |
| 6,300,753 | B1 | * | 10/2001 | Walde et al. .................. 324/71.1 |
| 6,656,337 | B2 | | 12/2003 | Kurokawa et al. |
| 6,994,780 | B2 | | 2/2006 | Mizutani et al. |
| 2002/0162743 | A1 | * | 11/2002 | Inagaki ......................... 204/425 |
| 2004/0050695 | A1 | | 3/2004 | Haraguchi et al. |
| 2004/0112765 | A1 | * | 6/2004 | Alkemade et al. ............. 205/784 |
| 2005/0173263 | A1 | * | 8/2005 | Bowden ........................ 205/775 |

FOREIGN PATENT DOCUMENTS
WO    WO9918430    * 4/1999
* cited by examiner

*Primary Examiner* — Kaj K Olsen
*Assistant Examiner* — Susan D Leong
(74) *Attorney, Agent, or Firm* — Julia Voutyras; Alleman Hall McCoy Russell & Tuttle LLP (57) ABSTRACT

A method is disclosed for operating an electrochemical gas sensor with a measuring electrode pair and a pumping electrode pair. The method includes obtaining a measurement of the interfering species at a location spatially adjacent to a measuring electrode of the measuring electrode pair; and adjusting one or more of an operation or an output processing of the electrochemical gas sensor based on the measurement of the interfering species. In this manner, the measurement of the interfering species may be used to adjust the removal rates of the interfering species and/or to adjust an offset of an analyte measurement to compensate for the presence of the interfering species.

19 Claims, 5 Drawing Sheets

SYSTEM AND METHOD FOR IMPROVING ACCURACY OF A GAS SENSOR

BACKGROUND AND SUMMARY

Electrochemical sensors may be used to monitor the concentrations of species in various environments. For example, an electrochemical NOx sensor may be used to detect the concentration of nitrogen oxide emissions (collectively "NOx") in the exhaust from an internal combustion engine. NOx sensors generally function by electrochemically dissociating NOx molecules and measuring a resulting ionic current through a solid electrolyte. Interfering species such as oxygen may be removed from the analytical environment within the sensor via electrochemical pumping to reduce the impact of such species on a NOx concentration measurement.

As NOx emission standards become more restrictive, sensor accuracy becomes increasingly important to provide accurate feedback for controlling processes and parameters related to emissions control. However, measuring low levels of NOx accurately can be difficult, as residual oxygen levels may cause offset errors in the NOx measurement. Furthermore, these effects may vary with oxygen concentration, water vapor concentration, electrode polarization effects due to sensor ageing and/or defects, etc.

The inventors herein have recognized that the accuracy of an electrochemical sensor such as a NOx sensor may be improved by obtaining a measurement of an interfering species at a location spatially adjacent to a measuring electrode of the measuring electrode pair, and adjusting one or more of an operation or an output processing of the electrochemical gas sensor based on the measurement of the interfering species. In this manner, the measurement of the interfering species may be used to adjust the removal rates of the interfering species and/or to adjust an offset of an analyte measurement to compensate for the presence of the interfering species.

DETAILED DESCRIPTION OF THE DEPICTED EMBODIMENTS

The present disclosure provides various embodiments of electrochemical gas sensors and various methods of operating electrochemical gas sensors that may help to reduce measurement errors caused by the presence of interfering species. Further, the sensors and methods disclosed herein may also help to compensate for variations in the offset and slope of the sensor output that occur over time due to electrode polarization effects arising from sensor ageing and other such factors.

The embodiments disclosed herein may help overcome such problems by electrochemically determining a concentration of an interfering species by measuring a Nernst voltage across an electrode pair due to the presence of the interfering species. The term "Nernst voltage" as used herein refers to the potential across an electrode that is in contact with an analytical sample and a reference electrode in the absence of an applied voltage. Without wishing to be bound by theory, in the absence of an applied voltage across the electrode pair, the electrode pair effectively may form a concentration cell with a voltage that is proportional to the difference in concentration of a desired species inside and outside of the sensor. The Nernst equation may then be used to determine the concentration of the species within the sensor from the measured voltage. In the specific example of a NOx sensor, a concentration of the interfering species oxygen may be determined in this manner. Then, based upon the measurement of residual oxygen in the sensor, an operation of and/or an output processing of the NOx sensor may be adjusted to compensate for the presence of the interfering species. Further, because the interfering species measurement may be continuously or periodically updated, variations in offset may be compensated for as well. The apparatus and methods disclosed herein may be used in any suitable sensor and/or application, including but not limited to the monitoring of species such as NOx in automotive exhaust.

Figure 1:
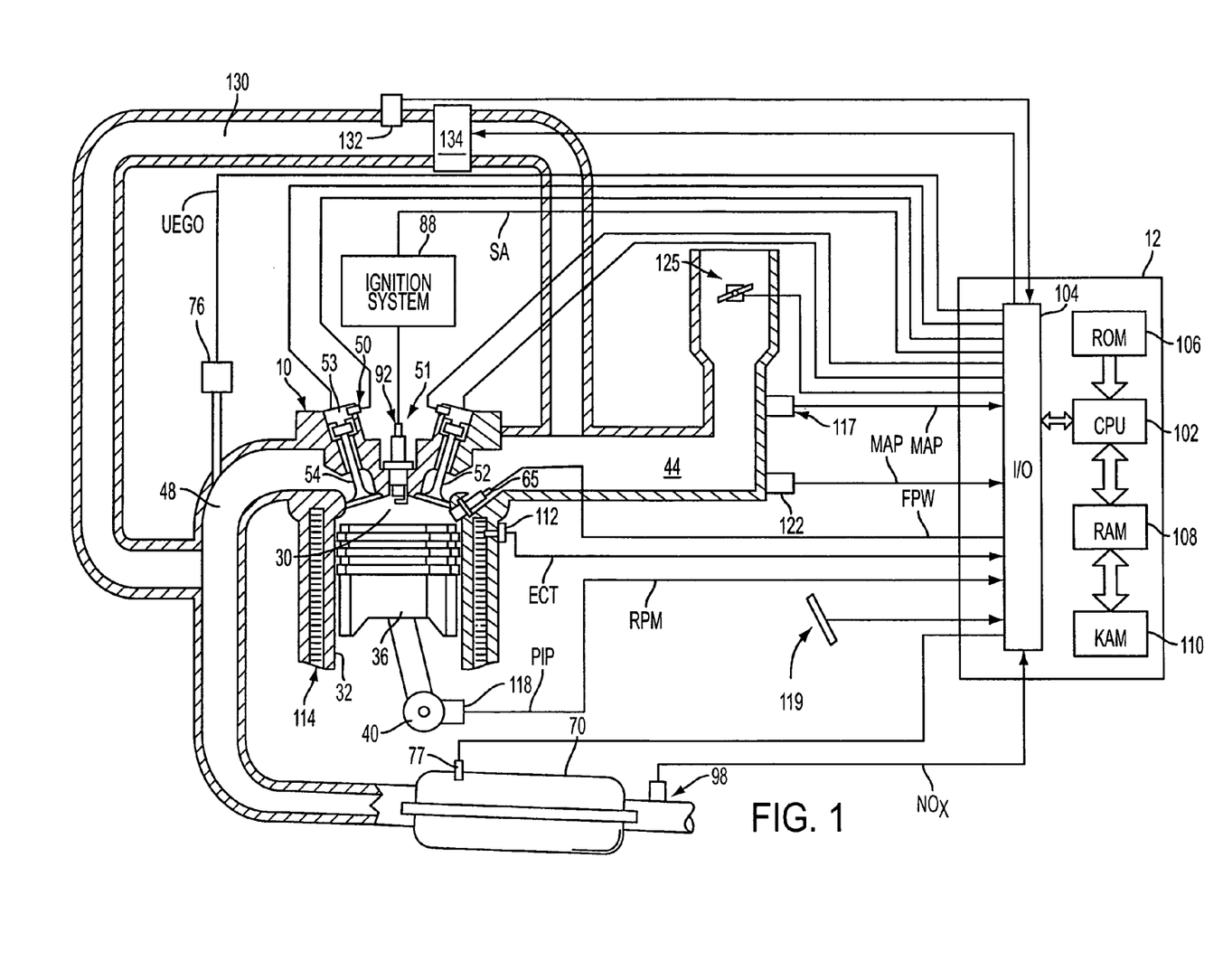
FIG. 1 is a schematic depiction of an exemplary embodiment of an internal combustion engine.

FIG. 1 shows an exemplary embodiment of an internal combustion engine 10, comprising a plurality of combustion chambers (one of which is indicated at 30), controlled by electronic engine controller 12. Combustion chamber 30 of engine 10 includes combustion chamber walls 32 with piston 36 positioned therein and connected to crankshaft 40. Combustion chamber 30 is shown communicating with intake manifold 44 and exhaust manifold 48 via respective intake valve 52 and exhaust valve 54. Fuel injector 65 is shown directly coupled to combustion chamber 30 for delivering liquid fuel directly therein in proportion to the pulse width of a signal (FPW) received from controller 12. However, in some embodiments, a fuel injector may be positioned in intake manifold 44, thereby providing port injection.

Intake air flow through intake manifold 44 may be adjusted with throttle 125, which is controlled by controller 12. An ignition spark may be provided to combustion chamber 30 via spark plug 92 in response to a spark signal from controller 12. Alternatively, spark plug 92 may be omitted for a compression ignition engine. Further, controller 12 may activate fuel injector 65 during the engine operation so that a desired air-fuel mixture is formed when ignition power is supplied to spark plug 92 by ignition system 88. Controller 12 controls the amount of fuel delivered by fuel injector 65 so that the air-fuel ratio mixture in chamber 30 may be selected to be substantially at (or near) stoichiometry, a value rich of stoichiometry, or a value lean of stoichiometry.

Intake valve 52 may be controlled by controller 12 via electric valve actuator (EVA) 51. Similarly, exhaust valve 54 may be controlled by controller 12 via EVA 53. During some conditions, controller 12 may vary the signals provided to actuators 51 and 53 to control the opening and closing of the respective intake and exhaust valves. The position of intake valve 52 and exhaust valve 54 may be determined by valve position sensors 55 and 57, respectively. In alternative embodiments, one or more of the intake and exhaust valves may be actuated by one or more cams, and may utilize one or more of cam profile switching (CPS), variable cam timing (VCT), variable valve timing (VVT) and/or variable valve lift (VVL) systems to vary valve operation. For example, cylinder 30 may alternatively include an intake valve controlled via electric valve actuation and an exhaust valve controlled via cam actuation including CPS and/or VCT.

Controller 12 is shown in FIG. 1 as a conventional microcomputer including: microprocessor unit 102, input/output ports 104, an electronic storage medium of executing programs and calibration values, shown as read-only memory chip 106 in this particular example, random access memory 108, keep alive memory 110, and a conventional data bus.

Controller 12 is shown receiving various signals from sensors coupled to engine 10, including: measurement of inducted mass air flow (MAF) from mass air flow sensor 117; accelerator pedal position from pedal position sensor 119; engine coolant temperature (ECT) from temperature sensor 112 coupled to cooling sleeve 114; a profile ignition pickup signal (PIP) from Hall effect sensor 118 coupled to crankshaft 40 giving an indication of engine speed (RPM); and absolute Manifold Pressure Signal (MAP) from sensor 122. Engine speed signal RPM is generated by controller 12 from signal PIP in a conventional manner and manifold pressure signal MAP provides an indication of engine load.

An exhaust gas recirculation (EGR) passage 130 is shown communicating with exhaust manifold 48 and intake manifold 44. The amount of EGR supplied to the intake manifold may be adjusted by EGR valve 134, which is in communication with controller 12. Further, controller 12 may receive a signal from EGR sensor 132, which may be configured to measure temperature or pressure of the exhaust gas within the EGR passage.

Exhaust gas oxygen sensor 76 is shown coupled to exhaust manifold 48 upstream of exhaust after-treatment system 70. Exhaust gas oxygen sensor 76 may be configured to provide a signal to controller 12, which indicates whether exhaust air-fuel ratio is either lean of stoichiometry or rich of stoichiometry. Exhaust after-treatment system 70 may include a catalytic converter, a lean NOx trap, and/or any other suitable treatment device. Exhaust after-treatment sensor 77 may be configured to provide a signal to controller 12 indicative of the condition of the exhaust after-treatment system 70 and may include measurement of temperature, pressure, etc.

A NOx sensor 98 is shown coupled to exhaust manifold 48 downstream of exhaust after-treatment system 70. NOx sensor 98 may be configured to output a signal to controller 12 in response to a detected concentration of NOx in the engine exhaust, as will be described in more detail below. NOx sensor 98 may also be configured to receive a signal from controller 12, such as a control signal for controlling a temperature of the sensor, a voltage applied to electrodes in the sensor, etc. In an alternative embodiment, sensor 98 may be configured to measure the concentration of other species besides NOx, including but not limited to $O_2$, CO, $H_2O$, SOx, and other oxygen-containing gases. NOx sensor 98 may be used both for control of the aftertreatment system and for on-board diagnostics (OBD) to ensure the vehicle does not exceed the NOx emissions standards.

Figure 2:
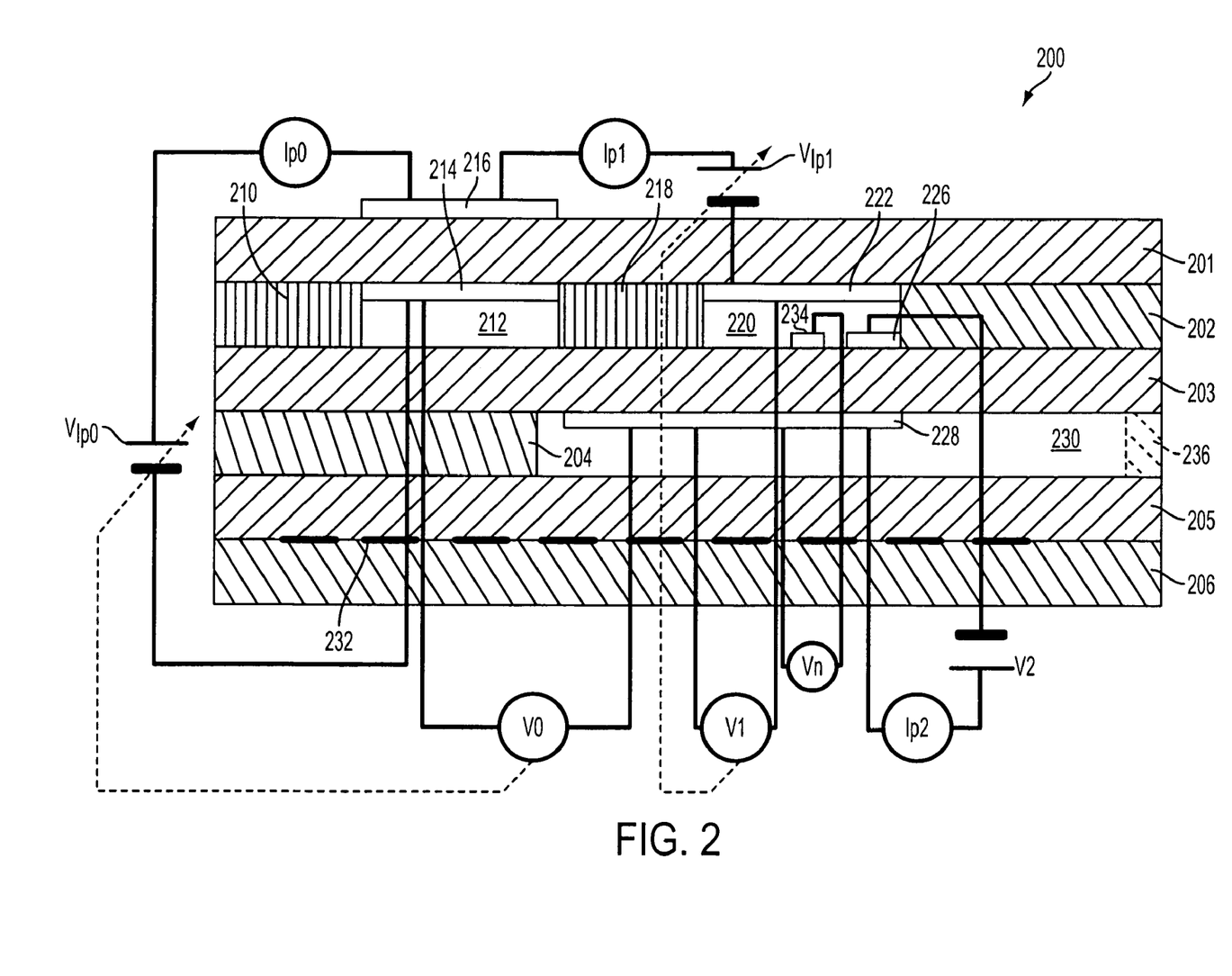
FIG. 2 is a schematic depiction of an embodiment of a NOx sensor.

FIG. 2 shows a schematic view of an exemplary embodiment of a NOx sensor 200 configured to measure a concentration of NOx gases in an emissions stream. Sensor 200 comprises a plurality of layers of one or more ceramic materials arranged in a stacked configuration. In the embodiment of FIG. 2, six ceramic layers are depicted as layers 201, 202, 203, 204, 205 and 206. These layers include one or more layers of a solid electrolyte capable of conducting ionic oxygen. Examples of suitable solid electrolytes include, but are not limited to, zirconium oxide-based materials. Further, in some embodiments, a heater 232 may be disposed between the various layers (or otherwise in thermal communication with the layers) to increase the ionic conductivity of the layers. While the depicted NOx sensor is formed from six ceramic layers, it will be appreciated that the NOx sensor may include any other suitable number of ceramic layers.

Layer 202 includes a material or materials creating a first diffusion path 210. First diffusion path 210 is configured to introduce exhaust gases into a first internal cavity 212 via diffusion. A first pair of pumping electrodes 214 and 216 is disposed in communication with internal cavity 212, and is configured to electrochemically pump a selected exhaust gas constituent from internal cavity 212 through layer 201 and out of sensor 200. Generally, the species pumped from internal cavity 212 out of sensor 200 may be a species that may interfere with the measurement of a desired analyte. For example, as mentioned above, molecular oxygen can potentially interfere with the measurement of NOx in a NOx sensor, as oxygen is dissociated and pumped at a lower potential than NOx. Therefore, first pumping electrodes 214 and 216 may be used to remove molecular oxygen from within internal cavity 212 to decrease the concentration of oxygen within the sensor relative to a concentration of NOx within the sensor.

First diffusion path 210 may be configured to allow one or more components of exhaust gases, including but not limited to the analyte and interfering component, to diffuse into internal cavity 212 at a limiting rate than the interfering component can be electrochemically pumped out by first pumping electrodes pair 214 and 216. In this manner, almost all of oxygen may be removed from first internal cavity 212 to reduce interfering effects caused by oxygen.

The process of electrochemically pumping the oxygen out of first internal cavity 212 includes applying an electric potential $V_{Ip0}$ across first pumping electrode pair 214, 216 that is sufficient to dissociate molecular oxygen, but not sufficient to dissociate NOx. With the selection of a material having a suitably low rate of oxygen diffusion for first diffusion path 210, the ionic current Ip0 between first pumping electrode pair 214, 216 may be limited by the rate at which the gas can diffuse into the chamber, which is proportional to the concentration of oxygen in the exhaust gas, rather than by the pumping rate of first pumping electrode pair 214, 216. This may allow a substantial majority of oxygen to be pumped from first internal cavity 212 while leaving NOx gases in first internal cavity 212. A voltage $V_0$ across first pumping electrode 214 and reference electrode 228 may be monitored to provide feedback control for the application of the electric potential $V_{Ip0}$ across first pumping electrode pair 214, 216.

Sensor 200 further includes a second internal cavity 220 separated from the first internal cavity by a second diffusion path 218. Second diffusion path 218 is configured to allow exhaust gases to diffuse from first internal cavity 212 into second internal cavity 220. A second pumping electrode 222 optionally may be provided in communication with second internal cavity 220. Second pumping electrode 222 may, in conjunction with electrode 216, be set at an appropriate potential $V_{Ip1}$ to remove additional residual oxygen from second internal cavity 220. Second pumping electrode 222 and electrode 216 may be referred to herein as a second pumping electrode pair. Alternatively, second pumping electrode 222 may be configured to maintain a substantially constant concentration of oxygen within second internal cavity 220. In some embodiments, ($V_{Ip0}$) may be approximately equal to ($V_{Ip1}$) while in other embodiments ($V_{Ip0}$) and ($V_{Ip1}$) may be different. While the depicted embodiment utilizes electrode 216 to pump oxygen from first internal cavity 212 and from second internal cavity 220, it will be appreciated that a separate electrode (not shown) may be used in conjunction with electrode 222 to form an alternate pumping electrode pair to pump oxygen from second internal cavity 220. A voltage V1 across second pumping electrode 222 and reference electrode 228 may be monitored to provide feedback control for the application of the electric potential $V_{Ip1}$ across second pumping electrode pair 222, 216.

First pumping electrode 212 and second pumping electrode 222 may be made of any suitable material. In some embodiments, first pumping electrode 212 and second pumping electrode may be at least partially made of a material that catalyzes the dissociation of molecular oxygen to the substantial exclusion of NOx. Examples of such materials include, but are not limited to, electrodes containing platinum and/or gold.

Sensor 200 further includes a measuring electrode 226 and a reference electrode 228. Measuring electrode 226 and reference electrode 228 may be referred to herein as a measuring electrode pair. Reference electrode 228 is disposed at least partially within or otherwise exposed to a reference duct 230. In one embodiment, reference duct 230 may be open to the atmosphere and may be referred as reference air duct. In another embodiment, reference duct 230 may be isolated by a layer 236 from the atmosphere such that oxygen pumped from second internal cavity 220 may be accumulated within the duct, thus reference duct 230 may be referred as oxygen duct.

Measuring electrode 226 may be set at a sufficient potential relative to reference electrode to pump NOx out of second internal cavity 220. Further, measuring electrode 226 may be at least partially made of a material that catalyzes dissociation or reduction of any NOx. For example, measuring electrode 226 may be made at least partially from platinum and/or rhodium. As NOx is reduced to $N_2$, the oxygen ions generated are electrochemically pumped from second internal cavity 220. The sensor output is based upon the pumping current flowing through measuring electrode 226 and reference electrode 228, which is proportional to the concentration of NOx in second internal cavity 220.

Sensor 200 further includes a calibration electrode 234. Calibration electrode 234 is used to measure the residual oxygen concentration in second internal cavity 220 according to a Nernst voltage (Vn) with reference to reference electrode 228. Thus, calibration electrode 234 and reference electrode 228 may be referred to herein as a calibration electrode pair. As shown in FIG. 2, calibration electrode 234 is disposed on the same solid electrolyte layer 203 as measuring electrode 226. Typically, calibration electrode 234 is disposed spatially adjacent to measuring electrode 226. The term "spatially adjacent" as used herein refers to the calibration electrode 234 being in the same volume of space (for example, second internal cavity 220) as measuring electrode 226. Furthermore, placing the calibration electrode 234 in close proximity to measuring electrode 226 may reduce the magnitude of any differences in oxygen concentration at the measuring electrode and at the calibration electrode due to an oxygen concentration gradient between the two electrodes. This may allow residual oxygen concentrations to be measured more accurately. Alternatively, calibration electrode 234 and measuring electrode 226 may be disposed on different solid electrolyte layers. For example, calibration electrode 234 may be disposed on solid electrolyte layer 201 instead of layer 203.

It will be appreciated that the depicted calibration electrode locations and configurations are merely exemplary, and that calibration electrode 234 may have any suitable location and configuration that allows a measurement of residual oxygen to be obtained. Further, while the depicted embodiment utilizes electrode 228 as a reference electrode of the calibration electrode pair, it will be appreciated that a separate electrode (not shown) may be used in conjunction with calibration electrode 234 to form an alternative calibration electrode pair configuration.

The measurement of the interfering species according to the Nernst voltage may offer various advantages. For example, the measurement of the Nernst voltage may be sensitive to small concentrations of residual oxygen that, while difficult to estimate accurately, nonetheless may significantly effect a NOx measurement. Extremely low concentrations of NOx may produce a pumping current on the order of nanoamperes. Therefore, even small concentrations of oxygen may greatly affect this result. The accurate determination of oxygen concentration may allow the offset of a NOx measurement caused by residual oxygen to be accurately determined and compensated for such that extremely low levels of NOx can be accurately measured. Further, the use of the Nernst voltage measurement of residual oxygen also may help to avoid oxygen measurement errors due to electrode polarization effects related to sensor ageing, electrode/electrolyte boundary defects, and electrolyte defects. Since no current is applied to the calibration electrode pair, polarization effects caused by applying a potential to the electrodes may be avoided. Thus, the effects of such electrode polarizations on the residual oxygen measurement may be substantially eliminated.

In some embodiments, calibration electrode 234 may be at least partially made of a material that catalyzes a dissociation of the oxygen to the exclusion of NOx. In this manner, the calibration electrode may dissociate oxygen to the substantial exclusion of NOx, and thereby may avoid errors in the residual oxygen measurement caused by the presence of NOx. In one example, a platinum and/or gold-containing electrode may be used. It should be noted that calibration electrode may include any suitable material that catalyzes a dissociation of an interfering species to the substantial exclusion of the gas species to be measured.

It should be appreciated that the NOx sensors described herein are merely example embodiments of NOx sensors, and that other embodiments of NOx sensors may have additional and/or alternative features and/or designs. For example, in some embodiments, a NOx sensor may include only one diffusion path and one internal cavity, thereby placing the first pumping electrode and measuring electrode in the same internal cavity. In such an embodiment, a calibration electrode may be disposed adjacent to the measuring electrode so that the residual oxygen concentration of an exhaust gas at or near the measuring electrode can be determined with a minimized impact from any oxygen concentration gradient.

Figure 3:
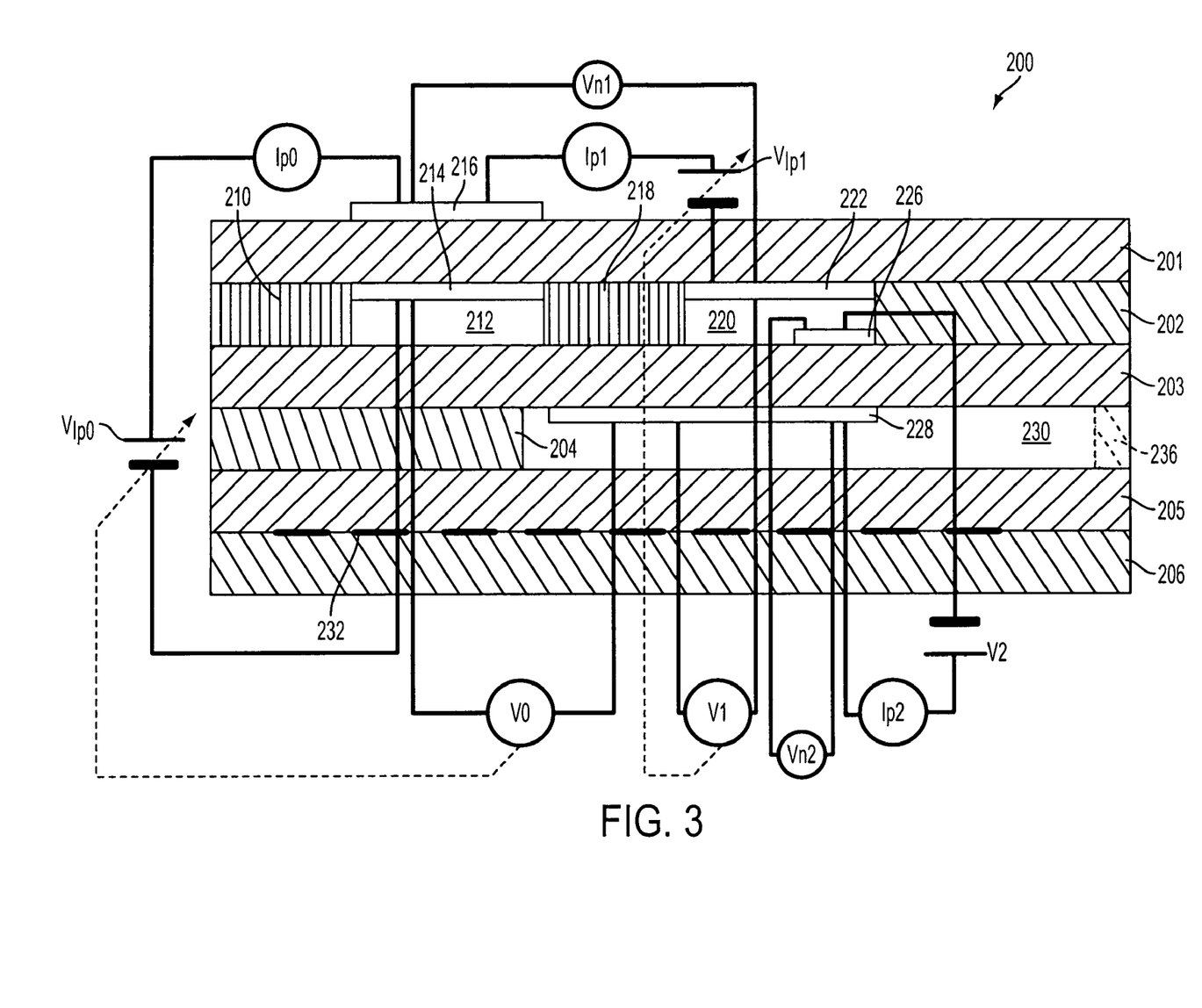
FIG. 3 is a schematic depiction of another embodiment of a NOx sensor.

FIG. 3 is a schematic depiction of another embodiment of a NOx sensor 300. As opposed to sensor 200, sensor 300 does not include a calibration electrode. Therefore, in the embodiment of FIG. 3, the pumping voltage ($V_{IP1}$) across either of second pumping electrode 222 or voltage (V2) across measuring electrode 226 may be temporarily turned off to measure a Nernst voltage caused by a concentration gradient of oxygen across the second pumping electrode pair (shown by $V_{n1}$), or across the measuring electrode pair (as shown by $V_{n2}$). Alternatively, voltage V1 may be used as a measure of the Nernst voltage across second pumping electrode 222. Thus, a separate voltage meter for measurement of $V_{n1}$ may not be required.

It should be understood that the exemplary embodiments of sensors described above with reference to FIGS. 2 and 3 are not intended to be limiting, and any other suitable sensor having any other configuration and/or materials may be used. Further, the methods disclosed herein may also be applied to sensors other than those used to detect NOx, including but not limited to CO, $CO_2$, SOx, and $H_2O$ sensors.

Figure 4:
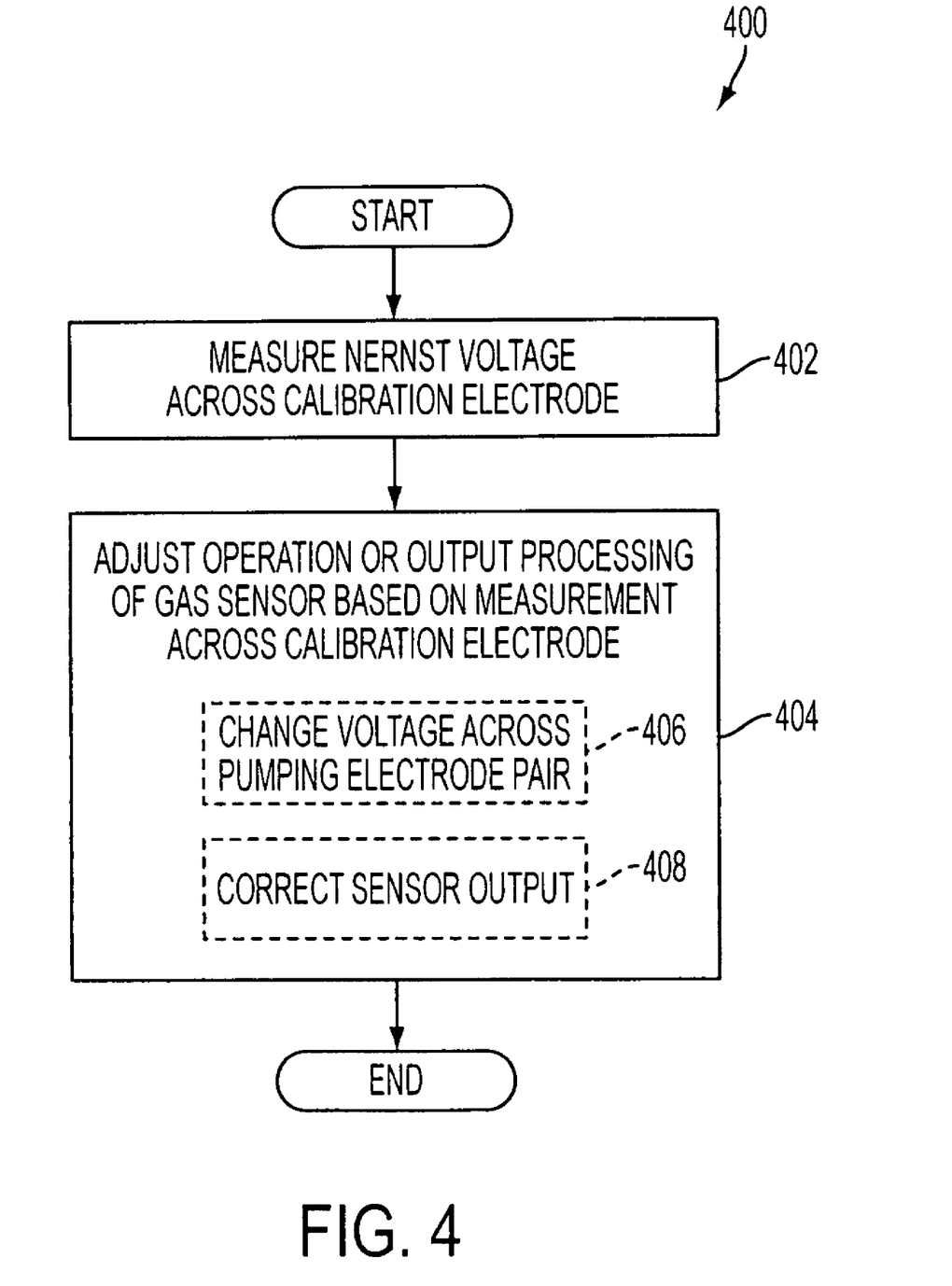
FIG. 4 is a flowchart showing an embodiment of a method of operating an electrochemical gas sensor.

FIG. 4 is a flowchart showing an exemplary method 400 of operating an electrochemical gas sensor according to one embodiment of the present disclosure. The embodiment of FIG. 4 may be used with a sensor having a calibration electrode, such as that depicted in FIG. 2. First, at 402, method 400 includes measuring a Nernst voltage across a calibration electrode pair to determine a concentration of an interfering species within the sensor. In the specific example of a NOx sensor, the interfering species may be oxygen. As described above, the calibration electrode may be disposed at a location spatially adjacent to a measuring electrode of the electrochemical sensor to reduce any inaccuracies caused by a potential concentration gradient of oxygen between the calibration electrode and measuring electrode. Therefore, the measure of the interfering species obtained at 402 may correspond to a concentration of oxygen within the sensor at the measuring electrode. As described above, various configurations of calibration electrodes pair are possible, including but not limited to that described above with reference to FIG. 2, and the scope of the present disclosure is not limited only to those calibration electrode configurations depicted and/or described.

Next, at 404, method 400 may include adjusting an operation or an output processing of the electrochemical gas sensor based on the measurement of the interfering species. The information from the measurement of the interfering species at 402 may be used in any suitable manner to compensate for the residual oxygen concentration. For example, in some embodiments, as indicated at 406, method 400 may include changing a voltage across one or more pumping electrode pairs to adjust a removal rate of the interfering species from the sample exhaust gas or the sensor. This may be employed, for example, where the output from the NOx sensor is calibrated to be accurate at a known residual oxygen concentration. Where the residual oxygen concentration is higher than the desired concentration, the pumping voltages at the pumping electrodes 214, 222 may be increased to increase pumping rates. Likewise, where the residual concentration is lower than the desired concentration, the pumping voltages may be decreased to lower pumping rates.

Likewise, the pumping voltages at electrodes 214, 222 may be increased during start-up conditions to lower the start-up time for a NOx sensor. For example, during periods of engine non-use, oxygen concentrations within the NOx sensor may rise such that the pumping rates of pumping electrodes 214, 222 are initially pumping rate limited, rather than being limited by the rate at which oxygen diffuses into the sensor chambers. Further, oxygen concentrations may be too great during this start-up phase to measure NOx concentrations with any sensitivity. Therefore, information from the measurement of the residual oxygen may be used as a feedback signal for adjusting a voltage applied to the pumping electrodes. In this manner, the measurement of the interfering species oxygen may allow an oxygen pumping voltage to be optimized for rapid oxygen removal, and then lowered as the oxygen concentration lowers to avoid damaging the sensor by the use of elevated pumping voltages for longer than necessary.

Continuing with FIG. 4, at 408, method 400 may alternatively or additionally include correcting or adjusting the output of the sensor based upon the measurement of the interfering species. For example, controller 12 may be configured to calculate a corrected sensor output by subtracting the interfering species concentration measured at the calibrating electrode from the output of the NOx sensor to compensate for any offset of the NOx sensor output signal caused by residual oxygen.

It should be appreciated that adjustment of the sensor operation at 406 and correction of the sensor output at 408 may be performed individually or collectively, and/or separately or concurrently. For example, the adjustment of the operation and output correction may be performed simultaneously to shorten start-up times. Further, it will be appreciated that these processes are merely examples of mechanisms in which a NOx sensor operation may be adjusted based upon a measured interfering species concentration, and that any other suitable mechanism to compensate for the interfering species concentration may be used.

Figure 5:
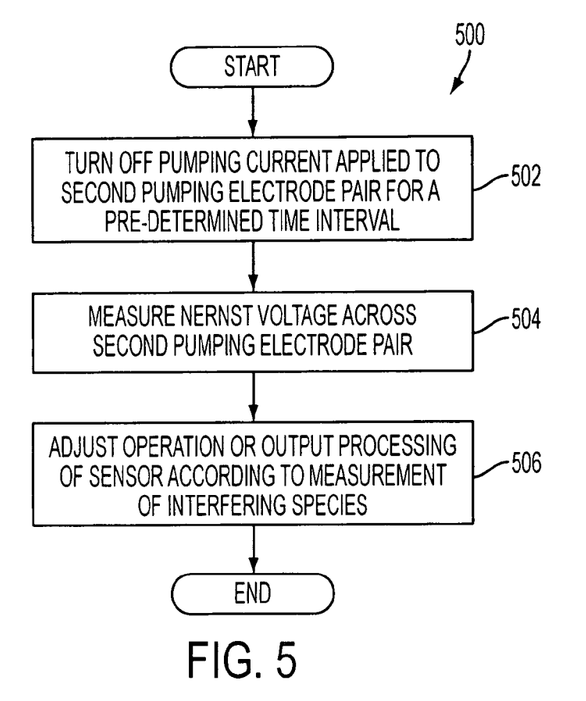
FIG. 5 is a flowchart showing another embodiment of a method of operating an electrochemical gas sensor.
Figure 6:
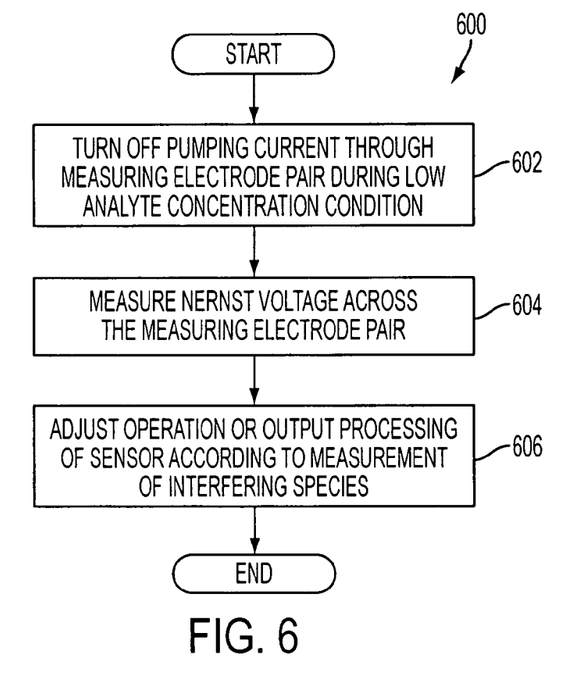
FIG. 6 is a flowchart showing another embodiment of a method of operating an electrochemical gas sensor.

In some embodiments, the measurement of the interfering species according to a Nernst voltage across an electrode pair may also be achieved without a calibration electrode by using either a pumping electrode or a measurement electrode to measure the interfering species concentration. FIGS. 5 and 6 show embodiments of methods of measuring an interfering species concentration using electrodes other than a calibration electrode. First, FIG. 5 shows a flow diagram of an embodiment of a method 500 of operating an electrochemical gas sensor in which an interfering species is measured at a pumping electrode. First, at 502, method 500 includes turning off a pumping voltage applied to a pumping electrode pair (such as pumping electrode pair 222, 216 in FIG. 3) for a predetermined time interval.

Next, at 504, method 500 includes measuring a Nernst voltage across the pumping electrode pair to determine an amount of interfering species in a second internal cavity. Since the pumping electrode pair is used to reduce the oxygen level in the second internal cavity, the measurement of the interfering species is performed intermittently in the embodiment of FIG. 5. The duration for measurement of the interfering species may be shorter than the duration for pumping interfering species to avoid accumulating excess concentrations of the interfering species, or may have any other suitable duration. For example, in some embodiments, the duration for measurement may be in a range of milliseconds. It will be appreciated that this is merely an example of a suitable range of measurement durations, and that measurements of any other suitable duration may be performed.

Likewise, the residual oxygen measurement may be made at any suitable frequency. In some embodiments, the frequency of residual oxygen measurement may depend on the predominant factors that may cause the oxygen measurement to vary. For example, if measurement variations are caused by ageing of the sensor, the offset may be relatively constant over a period of time at some conditions. Thus, the measurement of the residual oxygen may be performed less frequently. If oxygen measurement variations are caused by variations in the compositions of an exhaust gas such as water content, the offset may fluctuate over time as the gas species concentrations in the exhaust gas changes. Thus, the residual oxygen measurement may be performed more frequently.

Next, at 506, method 500 includes adjusting an operation or an output processing of the sensor according to the measurement of interfering species. Step 506 may be performed as described above with reference to FIG. 4.

Method 500 may offer the advantage that it may be used with sensors that do not have a calibrating electrode such as that shown at 234 in FIG. 2. Further, method 500 may offer the other advantages described with respect to the other embodiments above. For example, method 500 may permit an accurate measurement of the concentration of the interfering species to be made in the absence of an applied voltage, thereby potentially lessening electrode polarization effects.

Next, FIG. 6 is a flow diagram showing an embodiment of a method 600 of operating an electrochemical gas sensor in which an interfering species measurement is measured at a measuring electrode. First, at 602, method 600 includes turning off a pumping voltage across a measuring electrode pair for a predetermined time interval. If the Nernst voltage at the measurement electrode is affected by the presence on the analyte, it may be advantageous to perform the measurement when a concentration of an analyte is low (i.e. a "low analyte concentration condition"). For example, where NOx is the analyte in an exhaust stream from a vehicle, the low analyte concentration condition may correspond to a period where NOx output from the engine is low. Because the NOx measurement electrode is active or sensitive to NOx, the low NOx condition may be required to reduce the interference of NOx to the oxygen measurements. Such a low NOx concentration condition may occur under various conditions, such as during deceleration, coasting, and/or fuel cutoff of the vehicle.

Next, at 604, method 600 includes measuring a Nernst voltage across the measuring electrode pair to determine an amount of an interfering species in the environment around the measuring electrode. As described above, various sensors having various measuring electrode configurations are possible. FIG. 3 shows one exemplary embodiment of a sensor 300 in which method 600 may be implemented.

Next, at 606, method 600 includes adjusting an operation or an output processing of the sensor according to the measurement of interfering species. Step 606 may be performed as described above with reference to FIG. 4.

Method 600 may be used to reduce inaccuracy of oxygen measurement due to polarization effects arising from applying a voltage to an electrode. Further, the use of the NOx measuring electrode to measure the interfering species concentration may eliminate any potential errors that could result from an interfering species concentration gradient between the measuring electrode and a calibration or pumping electrode used to measure an interfering species.

It may be appreciated that the order of processing to be detailed is not necessarily required to achieve the features and advantages of the example embodiments described herein, but is provided for ease of illustration and description. One or more of the illustrated steps or functions may be repeatedly performed depending on the particular strategy being used. Further, the described steps may graphically represent code to be programmed into a computer readable storage medium for the sensor, for example, in the engine control system.

Furthermore, it will be appreciated that the various embodiments of gas sensors and methods of operating gas sensors disclosed herein are exemplary in nature, and these specific embodiments are not to be considered in a limiting sense, because numerous variations are possible. The subject matter of the present disclosure includes all novel and nonobvious combinations and subcombinations of the various sensors, methods of operating sensors, and other features, functions, and/or properties disclosed herein. The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the various features, functions, elements, and/or properties disclosed herein may be claimed through amendment of the present claims or through presentation of new claims in this or a related application. Such claims, whether broader, narrower, equal, or different in scope to the original claims, also are regarded as included within the subject matter of the present disclosure.

What is claimed here:

1. A method of operating an electrochemical gas sensor, the electrochemical gas sensor comprising a measuring electrode pair configured to measure a gas species and a pumping electrode pair configured to reduce an amount of an interfering species in a sample in the electrochemical gas sensor, the method comprising:
obtaining a measurement of the interfering species at a location spatially adjacent to a measuring electrode of the measuring electrode pair;
adjusting one or more of an operation or an output processing of the electrochemical gas sensor based on the measurement of the interfering species,
wherein measuring the interfering species comprises turning off a pumping current through the pumping electrode pair that pumps the interfering species out of the sample for a predetermined time interval, and determining the amount of the interfering species in the sample according to a Nernst voltage across the pumping electrode pair during the predetermined time interval.

2. The method of claim 1, wherein the pumping electrode pair is a first pumping electrode pair, the electrochemical gas sensor further comprising a second pumping electrode pair having a second pumping electrode and a reference electrode, and wherein measuring the interfering species further comprises:
turning off a pumping current through the second electrode pair for a predetermined time interval; and
determining the amount of the interfering species in the sample according to a Nernst voltage across the second pumping electrode pair.

3. The method of claim 1, wherein measuring the interfering species further comprises:
turning off a pumping current through the measuring electrode pair; and
determining the amount of the interfering species in the sample according to a Nernst voltage across the measuring electrode pair.

4. The method of claim 1, wherein adjusting the operation of the electrochemical gas sensor comprises increasing a voltage across the pumping electrode to increase a rate of removal of the interfering species from the sample.

5. The method of claim 1, wherein adjusting the output of the electrochemical gas sensor comprises correcting the output according to a measured amount of the interfering species.

6. The method of claim 1, wherein the electrochemical gas sensor further comprises a calibration electrode disposed spatially adjacent to the measuring electrode, and wherein measuring the interfering species further comprises determining the amount of the interfering species in the sample according to a Nernst voltage across the calibration electrode and a reference electrode.

7. The method of claim 6, wherein the calibration electrode is at least partially made of a material that catalyzes a dissociation of the interfering species to the substantial exclusion of the gas species to be measured.

8. A method of operating an electrochemical gas sensor in a vehicle, the vehicle comprising an internal combustion engine, the electrochemical gas sensor including a first internal cavity, a first pumping electrode pair configured to pump an interfering species out of the first internal cavity, a second internal cavity, a second pumping electrode pair configured to pump the interfering species out of the second internal cavity, and a measuring electrode pair configured to measure a gaseous species, the method comprising:
generating a pumping current that pumps the interfering species out of the second internal cavity through one or more of the second pumping electrode pair and the measuring electrode pair;

turning off the pumping current that pumps the interfering species out of the second internal cavity through the one or more of the second pumping electrode pair and the measuring electrode pair; and measuring the interfering species based on a Nernst voltage across the one or more of the second pumping electrode pair and the measuring electrode pair.

9. The method of claim 8, wherein turning off the pumping current through the second pumping electrode pair comprises turning off the pumping current at a predetermined time interval.

10. The method of claim 9, wherein the predetermined time interval varies based on a condition of the electrochemical gas sensor.

11. The method of claim 10, wherein the condition is one of an ageing of the electrochemical gas sensor and a water content of an exhaust gas from the internal combustion engine.

12. The method of claim 8, wherein turning off the pumping current through the measuring electrode occurs at a vehicle condition where an amount of the gaseous species in an exhaust of the internal combustion engine is determined to be low.

13. The method of claim 12, wherein the gas species is NOx.

14. The method of claim 13, wherein the interfering species is oxygen and the vehicle condition is a low NOx condition.

15. The method of claim 14, wherein the low NOx condition is one of a deceleration of the vehicle, a coasting of the vehicle, and fuel cutoff in the engine.

16. The method of claim 8, further comprising adjusting a voltage across one of the first pumping electrode pair and the second pumping electrode pair according to a measured amount of the interfering species.

17. The method of claim 16, wherein adjusting the voltage comprises increasing the voltage across the first pumping electrode pair according to a measured amount of the interfering species such that a start-up time for the electrochemical gas sensor is shortened.

18. The method of claim 16, further comprising calculating an offset of the electrochemical gas sensor based on measurement of the interfering species.

19. A method of operating an electrochemical gas sensor comprising a measuring electrode pair configured to measure NOx and a pumping electrode pair configured to reduce an oxygen amount in a sample in the electrochemical gas sensor, comprising:

obtaining a measurement of the oxygen at a location spatially adjacent to a measuring electrode of the measuring electrode pair, including turning off a pumping current through the pumping electrode pair that pumps the oxygen out of the sample for a predetermined time interval, the oxygen amount determined according to a Nernst voltage across the pumping electrode pair during the predetermined time interval; and adjusting an output processing of the electrochemical gas sensor based on the measurement of the oxygen.

* * * * *